United States Patent [19]

Abramson et al.

[11] Patent Number: 4,465,637

[45] Date of Patent: Aug. 14, 1984

[54] ALKYL VANADATE COLOR IMPROVEMENT

[75] Inventors: Alan J. Abramson; Gershon J. Davis, both of White Plains, N.Y.

[73] Assignee: Stauffer Chemical Company, Westport, Conn.

[21] Appl. No.: 416,818

[22] Filed: Sep. 13, 1982

[51] Int. Cl.$^3$ .................................................. C07F 9/00
[52] U.S. Cl. ................................................. 260/429 R
[58] Field of Search .................................... 260/429 R

[56] References Cited

U.S. PATENT DOCUMENTS

| | | | |
|---|---|---|---|
| 1,133,961 | 3/1915 | Hess | 260/429 R |
| 2,220,041 | 10/1940 | Hill | 260/429 R |
| 2,257,009 | 9/1941 | Hill | 260/429 R |
| 3,652,617 | 3/1972 | Termin et al. | 260/429 R |
| 3,657,295 | 4/1972 | McCoy | 260/429 R |
| 3,920,751 | 11/1975 | Chabardes et al. | 260/429 R |
| 3,987,074 | 10/1976 | Haase et al. | 260/429 R |
| 4,014,911 | 3/1977 | Muntz et al. | 260/429 R |
| 4,014,912 | 3/1977 | Muntz et al. | 260/429 R |
| 4,351,775 | 9/1982 | Magee | 260/429 R |

*Primary Examiner*—Helen M. S. Sneed
*Attorney, Agent, or Firm*—Richard P. Fennelly

[57] ABSTRACT

The color of alkyl vanadate compounds that have become discolored is improved by treating the vanadates with an oxygen-containing gas, e.g., air, preferably at elevated temperature.

7 Claims, No Drawings

ALKYL VANADATE COLOR IMPROVEMENT

BACKGROUND OF THE INVENTION

1. Field of the Invention

The present invention relates to the color improvement of alkyl vanadates.

2. Description of the Prior Art

Various methods are known for the preparation of alkyl vanadates. U.S. Pat. No. 4,014,912 to R. L. Muntz et al. describes reaction of vanadium oxytrichloride with an alcohol in the presence of ammonia and a hydrocarbon solvent with the later addition of dimethyl sulfoxide. The reaction is conducted under an inert gas atmosphere to prevent decomposition of the product. A variation of this process, in which an amide is added, rather than dimethyl sulfoxide, is described in U.S. Pat. No. 4,014,911 to R. L. Muntz et al. In this patent it is suggested that a stream of inert gas be passed through the reaction mixture to sweep out a portion of the hydrogen chloride by-product released by the reaction.

Alkyl vanadates are formed by reaction of vanadium pentoxide and an alkyl alcohol in a process described in U.S. Pat. No. 3,657,295 to D. R. McCoy. Once again, this patent indicates use of an inert atmosphere to prevent decomposition of the product.

In U.S. Pat. No. 3,987,074 to R. Haase et al. alkyl vanadates are described as being prepared by reaction of vanadium pentoxide and an alcohol in the presence of a particular orthoester to assist in the removal of by-product water. This patent indicates that vanadium pentoxide reagent remaining after the reaction can be regenerated and restored to full reactivity by thermal treatment, e.g., at 300°–400° C., under air or oxygen.

SUMMARY OF THE PRESENT INVENTION

The present invention is a process for color improvement of alkyl vanadate compounds which have at least partially decomposed. It comprises treating the alkyl vanadate with a stream of oxygen-containing gas, preferably at elevated temperature, to achieve the desired degree of color improvement.

DESCRIPTION OF THE PREFERRED EMBODIMENTS

Alkyl vanadates, which have become discolored due to chemical decomposition, can have their color improved by treatment with an oxygen-containing gas, e.g., air or substantially pure oxygen, under conditions which result in said color improvement. Preferably, the treatment with such gas is conducted at elevated temperature, e.g., 20° C. to 110° C. The rate of gas flow and time of treatment are inversely proportional to one another and can be varied widely. Representative gas flow rates range from about 200 liters of air per hour per liter of vanadate to about 50 liters of air/hr/liter of vanadate with treatment times of from about 0.1 hour to about 5 hours.

The present invention is further illustrated by the Examples which follow.

EXAMPLE 1

Triisobutyl vanadate having a brownish color was placed in a 500 ml. three-neck flask equipped with a sintered glass sparging tube, magnetic stir-bar and thermometer. Air was passed through a DRIERITE drying tube to eliminate water. The air was bubbled into the vanadate at the rate of 56.63 liters of air per hour at a temperature of 95°–105° C. for about 1 hour at the end of which time an improvement in color was noted.

EXAMPLE 2

The previous run was repeated using a composite sample of 412.1 gm. of dark, opaque triisobutyl vanadate from various pilot plant runs. The Table sets forth the results:

| Time | Temp. (°C.) | Comments |
|---|---|---|
| Start | 20 | Sparging and heating begun. |
| 42 min. | 73 | Slight clearing - thermometer visible. |
| 52 min. | 97.5 | More improvement - sparge tube visible. |
| 56 min. | 99 | Stir bar visible. |
| 97 min. | 100 | Transparent, slightly dirty yellow solution. |

COMPARATIVE EXAMPLE 3

This illustrates the inferior results obtained by sparging with nitrogen, rather than air as the oxygen-containing gas.

The process of Example 2 was repeated using nitrogen rather than air:

| Time | Temp. (°C.) | Comments |
|---|---|---|
| Start | 21 | Sparging and heating started. |
| 20 min. | 84 | Slight clearing noted. |
| 32 min. | 99 | No improvement. |
| 58 min. | 101 | No improvement. |
| 88 min. | 102 | No improvement over starting mixture. |

The present invention is a useful technique for color improvement of the alkyl vanadates which contain up to about 6 carbon atoms in their alkyl groups. Color improvement is desired in those applications (e.g., plasticizer applications) in which the vanadate is added to other materials and the resulting product is intended to retain the original color of the material.

The foregoing Examples illustrate certain preferred embodiments of the present invention and should not be construed in a limiting sense. The scope of protection that is sought is set forth in the claims which follow.

What is claimed:

1. A process for the color improvement of an alkyl vanadate which comprises treating the alkyl vanadate with a stream of an oxygen-containing gas to achieve the color improvement.

2. A process as claimed in claim 1 wherein the treating takes place at a temperature of from about 20° C. to about 110° C.

3. A process as claimed in claim 1 wherein the treating takes place at the rate of from about 50 liter air/hr./liter vanadate to about 200 liter air/hr./liter vanadate.

4. A process as claimed in claim 1 in which the treating takes place during a period of from about 0.1 to about 5 hours.

5. A process as claimed in claim 1 in which the treating takes place at a temperature of from about 20° C. to about 110° C. with an air flow of from about 50 to about 200 liters or air/hr./liter vanadate.

6. A process as claimed in claim 5 wherein the treating takes place from about 5.0 to about 0.1 hours.

7. A process as claimed in any of claims 1–6 wherein the oxygen-containing gas is air.

* * * * *

UNITED STATES PATENT AND TRADEMARK OFFICE
CERTIFICATE OF CORRECTION

PATENT NO. : 4,465,637
DATED : August 14, 1984
INVENTOR(S) : Alan J. Abramson; Gershon J. Davis It is certified that error appears in the above—identified patent and that said Letters Patent is hereby corrected as shown below:

Col. 2, line 63, "or" after "200 liters" should be -- of --.

Signed and Sealed this

Fifth Day of February 1985

[SEAL]

Attest:

DONALD J. QUIGG

Attesting Officer    Acting Commissioner of Patents and Trademarks